US006649798B2

(12) United States Patent
Klein et al.

(10) Patent No.: US 6,649,798 B2
(45) Date of Patent: Nov. 18, 2003

(54) METHOD FOR PRODUCTION OF DIAMINODIPHENYLMETHANES

(75) Inventors: Stephan Klein, Bergisch Gladbach (DE); Dirk Grotjohann, Leverkusen (DE); Christine Mendoza-Frohn, Erkrath (DE); Daniel Koch, Duisburg (DE); Heinz-Herbert Müller, Krefeld (DE); Hans-Georg Pirkl, Leverkusen (DE); Rudolf Uchdorf, Krefeld (DE); Gerhard Wegener, Mettmann (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/203,250
(22) PCT Filed: Feb. 1, 2001
(86) PCT No.: PCT/EP01/01083
§ 371 (c)(1), (2), (4) Date: Aug. 7, 2002
(87) PCT Pub. No.: WO01/58847
PCT Pub. Date: Aug. 16, 2001

(65) Prior Publication Data
US 2003/0023116 A1 Jan. 30, 2003

(30) Foreign Application Priority Data
Feb. 14, 2000 (DE) .......................................... 100 06 452

(51) Int. Cl.$^7$ .............................................. C07C 211/00
(52) U.S. Cl. ....................................... 564/332; 564/331
(58) Field of Search ................................. 564/332, 331

(56) References Cited

U.S. PATENT DOCUMENTS

| | | | |
|---|---|---|---|
| 3,860,637 A | 1/1975 | Bentley | 260/570 D |
| 4,011,278 A | 3/1977 | Plank et al. | 260/682 |
| 4,039,581 A | 8/1977 | Frulla et al. | 260/570 D |
| 4,172,847 A | 10/1979 | Marquis et al. | 260/570 D |
| 5,241,119 A | 8/1993 | Clerici et al. | 564/332 |

FOREIGN PATENT DOCUMENTS

EP  0 329 367  8/1989

*Primary Examiner*—Samuel Barts
(74) *Attorney, Agent, or Firm*—Joseph C. Gil; N. Denise Brown

(57) ABSTRACT

The present invention concerns a process for the production of methylenedianiline (MDA) having a high monomer content.

7 Claims, No Drawings

METHOD FOR PRODUCTION OF DIAMINODIPHENYLMETHANES

BACKGROUND OF THE INVENTION

The present invention concerns a process for the production of methylenedianiline (MDA) with a high monomer content and low ortho content by rearrangement of a condensation product (known as aminal or N,N-diphenylmethylenediamine) from aniline and formaline or another suitable methylene group-supplying agent such as trioxan or p-formaldehyde, catalysed on solid acids.

MDA (particularly the 4,4'-isomer) is an extremely suitable starting material from which—optionally after further purification—diisocyanates that represent an important raw product for polyurethane systems, for example, can be obtained by phosgenation. At the same time, the aliphatic systems that are obtained from MDA by hydrogenation of the aromatic ring also play an important role as paint resins.

Of the many conceivable methods described in the literature for the production of MDA, manufacture from the aniline-formaldehyde condensation product (known as aminal) is the most important because it is the most economically advantageous. Depending on the variant, the condensation product is produced first and then rearranged in the presence of (mostly) mineral acids such as HCl or alternatively the condensation itself is performed in the presence of acids under rearrangement conditions.

The disadvantages of such methods in regard to the synthesis of monomeric MDA can be summarised as follows: depending on the reaction conditions, the methods lead to mixtures consisting of excess aniline, MDA monomer (2,2'-, 2,4'- and 4,4'-isomeric) and polynuclear compounds (known as polymer bases), from which the monomeric MDA—optionally after conversion to the corresponding isocyanates—can be obtained. A preparation consisting of almost polymer-free MDA bases can be obtained only with extreme excesses of aniline in comparison to the methylene group-supplying agent, leading to low space-time yields and large circulating flows of aniline.

A further disadvantage of the preparation by catalysis of mineral acids is the accumulation of salt-containing waste waters that occur during neutralisation of the acid. Moreover, aqueous mineral acids lead to corrosion problems in plants.

A whole series of suggestions for the industrial implementation of the rearrangement, including the use of solid acids, has therefore already been made in order to overcome these disadvantages.

However, a feasible method for the production of MDA monomer bases avoiding mineral acids must meet the following conditions, for example:

a) Quantitative yields: an intermediate-free (aminobenzylaniline-free) product must be obtained in order to ensure that it is capable of being phosgenated (these can be extremely troublesome in the subsequent processing of the MDA to MDI (phosgenation).

b) Isomer distribution: similarly to the mineral acid-catalysed method, the product composition must be able to be controlled to some extent by varying the process parameters.

c) Service life: a catalyst used in industry must achieve an economic service life with high space-time yields before its activity can be restored by means of regeneration.

d) Foreign substances: the catalyst used must release no trace components in the product that have a negative influence on product quality. In addition, the method must cause no foreign matter, e.g. in the form of a solvent that is foreign to the system, to be brought into the reaction mixture.

Various attempts to obtain the pure binuclear molecule selectively have already been described, whereby a distinction has to be made between (a) methods for the material separation of mixtures of isomers and homologues and (b) the selective synthesis of the binuclear compounds:

(a) Methods for selective 4,4'-MDA crystallisation from halogenated solvents were described for example in U.S. Pat. No. 4,172,847. The disadvantage of this process, however, is that a foreign solvent has to be used in a complex additional process step, as a result of which additional material cycles and separating operations are required.

(b) U.S. Pat. No. 4,011,278 reports on numerous conversions of polar organic compounds using ZSM-5 zeolites and other zeolite types. It also mentions the conversion of N-alkylaniline with formaldehyde in the presence of zeolitic catalysts, without making any reference to reaction conditions, yields and selectivities, however.

It is known from DE-A-2 202 500 that if aminal is rearranged using amorphous silicon-aluminium-mixed oxide cracking catalysts, high yields of 4,4'-isomers are obtained if the reaction is itself performed in the presence of ortho isomers (obtained from another batch, for example). No additional proportions of 2,2'- and 2,4'-MDA are obtained in the presence of these isomers, since after their primary formation they preferentially react to higher-functional oligomeric MDA grades. A high proportion of polymer bases is therefore conventionally obtained, which have to be separated off from the desired 4,4'-isomer. Furthermore, this process requires the o-isomers formed to be recycled as an additional step.

It would be more advantageous to establish conditions during the actual synthesis of MDA that ensure high proportions of 4,4'-MDA, whereby the above-mentioned problems of salts and corrosion can be circumvented at the same time by synthesis using solid acids.

Thus it has already become known from the above-mentioned U.S. Pat. No. 4,011,278 that high selectivities in terms of the binuclear compound and particularly of 4,4'-MDA can sometimes be obtained using solid oxidic acids, for example, but particularly using zeolites.

EP-A-0 264 744 describes the condensation of aniline with trioxan or free formaldehyde and the rearrangement to MDA bases using solid boron-containing zeolites. Simultaneous condensation and rearrangement as well as isolation of aminobenzylanilines with subsequent rearrangement to MDA were both performed. Although high monomer selectivities were obtained by rearrangement of the aminobenzylanilines to MDA (approx. 90 mol % binuclear isomers in the aniline-free mixture), a complete conversion was not achieved and furthermore the reaction is preferably performed in benzene as solvent.

Attempts have also already been made to perform the rearrangement of aminal via aminobenzylaniline to MDA according to the prior art in several steps, for example in two steps, using solid acids in more than one step. U.S. Pat. No. 4,039,581 describes the rearrangement of an aminal from formaldehyde and aniline using solid acids, whereby it is first dried and then rearranged using zeolites, for example, in several reaction stages—characterised by temperature stages. A temperature of 100° C. is not exceeded, however, since it is assumed that high temperatures in the presence of water would be damaging to selectivity. A full rearrangement of the amino-benzylaniline intermediates to the MDA bases cannot be achieved under these conditions. An MDA with a binuclear content of approx. 90 mol % in the aniline-free mixture is obtained as product.

EP-A-0 329 367 describes the rearrangement of a dried aminal using zeolitic catalysts for the purpose of selective production of binuclear MDA. An aminal is rearranged isothermally at 120° C. using dealuminised HY zeolites and fluorinated derivatives thereof to a blend of MDA, which although consisting of approx. 94 mol % (relative to aniline-free solution) of binuclear MDA is characterised by incomplete conversion of the intermediates to the MDA bases. Approx. 5 mol % polymer bases are additionally formed.

SUMMARY OF THE INVENTION

The object of the present invention was therefore to find a process by which, contrary to the opinion represented in the literature, the conversion of aminal to low-polymer binuclear MDA can be performed using solid acid catalysts and thereby to utilise the advantages of catalysis with solids with sufficiently long catalyst residence times such as are required for industrial processes, without obtaining significant residual quantities of polymeric MDA bases or incompletely rearranged intermediates (aminobenzylanilines) in the end product.

This object is achieved according to the invention by a process for the production of methylenedianilines by the rearrangement of a condensation product consisting of aniline and a methylene group-supplying agent, e.g. formaldehyde, wherein a dried condensate of aniline and the methylene group-supplying agent having a molar ratio of aniline to methylene group-supplying agent of 1.7 to 100 is reacted under gentle conditions in the presence of solid, acid catalysts to low-polymer methylenedianiline with a predominant content of 4,4'-isomer, characterised in that aniline is used that is largely free from aliphatic amines.

Low-polymer methylenedianiline in the sense of the invention consists of at least 80 wt. %, preferably 85 wt. %, particularly preferably at least 90 wt. %, of binuclear compounds, of which the ortho isomer content makes up a maximum of 20 wt. %, preferably a maximum of 18 wt. %, particularly preferably a maximum of 16 wt. % and the content of 4,4'-isomers is a minimum of 80 wt. %, preferably a minimum of 82 wt. %, particularly preferably a minimum of 84 wt. %.

It follows from this that the content of 4,4'-isomers in the aniline-free overall mixture is between 64 and 100 wt. %. This is the definition of the predominant content of 4,4'-isomer in the low-polymer methylenedianiline.

This process can be illustrated in idealised form by means of the following diagram:

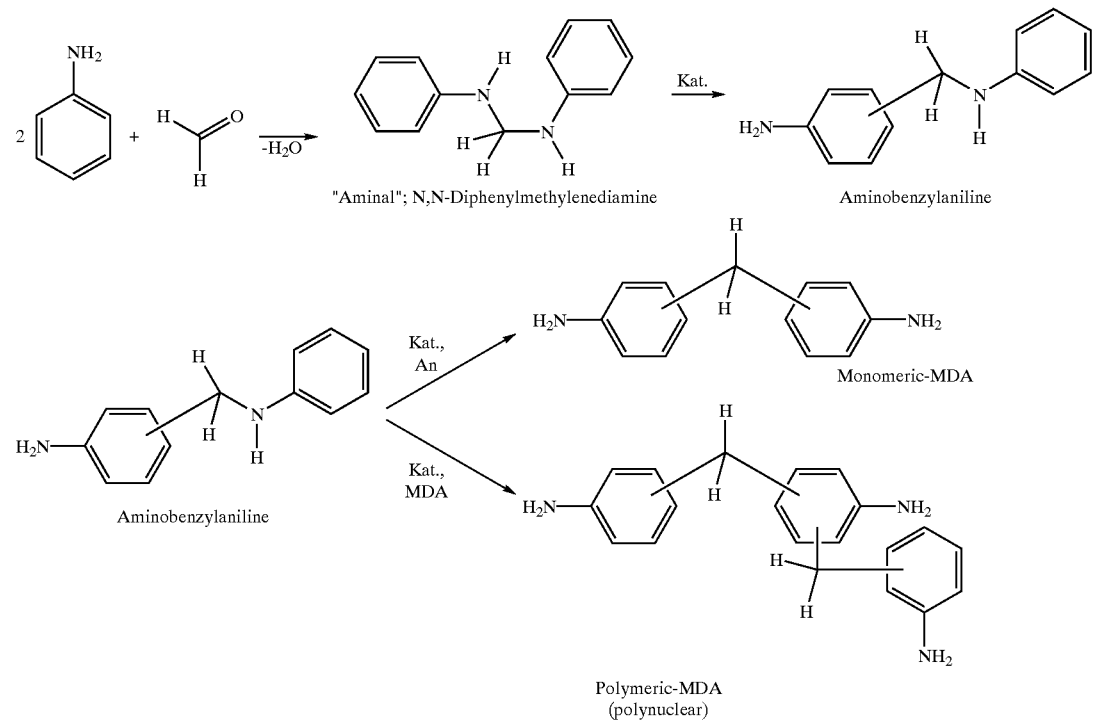

Examples of methylene group-supplying compounds in the sense of the invention include, in addition to aqueous formaldehyde solution, p-formaldehyde and trioxan. These are reacted with aniline, whereby a condensation product is formed that can be given the alternative name of aminal and consists predominantly of N,N-diphenylmethylenediamine. This condensation product is first dehydrated before the further reaction is performed under catalysis.

In principle the reaction to aminal can also be performed in the presence of a catalyst that causes the rearrangement to ABA and/or the MDA isomers. However, the water that is released during the condensation reaction reduces the activity and selectivity of the catalyst, as a consequence of which the successive version (aminal reaction→dehydration→rearrangement) is preferred.

The aminal reaction is preferably performed continuously by metering aniline and formaldehyde solution in a molar ratio of aniline to formaldehyde of 1.7 to 100, preferably 2 to 50, particularly preferably 4 to 20, into a reactor, from which a reaction quantity of the same volume as the feed stream is continuously removed and sent for phase separation. A batchwise or semi-continuous process is also conceivable, whereby the aniline and formaline are metered in the desired mixing ratio into a stirred batch reactor, from which the aminal that is reacted out is then sent for drying.

Dehydration can be performed both over dehydrating agents conventionally used in industry (e.g. molecular sieve), either continuously or batchwise, or azeotropically, for example, by means of continuous or batchwise distillation (dehydration with the aid of the aniline already present in the system). The aniline that may optionally be drawn off during the course of the process can conveniently be added in excess right at the beginning of the aminal reaction in order to obtain the desired ratio of aniline to aminal after drying by distillation.

The desired ratio of aniline to formaldehyde (A/F) for the rearrangement can be set at the time of the aminal reaction, optionally taking the drying losses into consideration. In principle, however, it is also possible to perform the aminal reaction and aminal dehydration at a low molar A/F of 1 to 5 and then to set the desired value of 4 to 20 immediately before the rearrangement using pure, dry aniline. The latter option allows the use of smaller apparatus at the aminal reaction and drying stages, leading to lower investment costs. Aniline recovered from reprocessing of the reaction mixture (recycled aniline) can also be used for restocking after condensation, which in the case of the operation using an excess of aniline is recovered from the fully rearranged MDA.

Drying by distillation is preferably performed continuously and under reduced pressure in order to subject the condensation product to the lowest possible thermal stress.

Dehydration is preferably performed down to a content of less than 1000 ppm water, particularly preferably less than 500 ppm water.

The catalysed rearrangement of the condensation product (aminal) must lead entirely to the desired MDA. Complete conversion is deemed to have been achieved when the intermediates have been reacted off down to a residual concentration of 0 to <500 mg/kg, preferably <200 mg/kg, of ABA.

Since the secondary products (in other words, different isomer compositions) of MDA are used in various applications, flexibility in the isomer composition is particularly important for industrial use. The isomer composition is substantially controlled by varying the reaction temperature and the catalyst type.

A distinction is therefore made between the first reaction phase (a), which governs selectivity, and the phase that serves to complete the conversion (b), whereby with the selected catalyst type the ratio of the temperature in the reaction phases determines the final composition in respect of o- and p-isomer contents. The lower the temperature in phase (a) that is selected between 0 and 70° C., the higher the content of p-isomers that can be achieved. Conversely, high temperatures in phase (a) of between 70 and 200° C. lead to high contents of o-isomers in the reaction mixture.

In the second reaction phase (b) the temperature is adjusted to an elevated level, preferably 100 to 200° C., in order to terminate the reaction completely and to break down the intermediates.

The catalysts used according to the invention must meet the following requirements:

Inorganic, preferably oxidic, particularly preferably siliceous catalysts are used.

Thus, for example, a commercially available Y-type zeolite (Faujasit) with a modulus ($SiO_2/Al_2O_3$) of 5 to 200 is used as catalyst, to which a binder (e.g. aluminium oxide) can be added for the purposes of moulding. The catalysts are preferably in the $H^+$ form. This can optionally be achieved by known methods (acid treatment, ammonium ion exchange followed by heat treatment).

The catalysts can in principle be used both in powder form and in lump form, whereby the conventional industrial processes of tabletting, pelletising or extrusion, for example, can be used for moulding, optionally with the aid of moulding additives. For industrial use in the continuous process, the catalyst is preferably used after moulding to run solid catalyst beds. In batchwise operation the catalysts are preferably used in quantities of 0.1 to 1000 wt. % relative to the catalyst-free reaction mixture, in continuous operation preferably in quantities of 0.01 to 100 kg catalyst/(kg aminal·h), especially preferably in quantities of 0.1–10 kg catalyst/(kg aminal·h).

Different grades and geometries, etc. of catalysts can also be used during the course of the process.

The process according to the invention is preferably performed in the absence of solvents.

It has also been found that suitable inorganic catalysts, such as zeolitic catalysts for example, can be severely deactivated by the proportions of aliphatic amines contained in the aniline. For example, technical aniline contains considerable proportions of these by-products (e.g. cyclohexylamine, dicyclohexylamine), which already lead to a significant deactivation. Technical aniline is obtained in industry by distillation of crude aniline.

For the process according to the invention, aniline grades are therefore preferably used that are largely free from aliphatic amines as minor and trace constituents (e.g. cyclohexylamine, dicyclohexylamine). For the process according to the invention, aniline with a purity of $\geq 99.5$ % is preferably used, whereby aniline grades with aliphatic amine contents (e.g. cyclohexylamine, dicyclohexylamine) of less than 100 ppm are preferred. Aniline grades with aliphatic amine contents of 0 to <25 ppm are particularly preferably used. Aliphatic amines can advantageously be removed from aniline by adsorption, preferably chemisorption, or acid washing.

The rearrangement according to the invention is performed with the dried aminal in such a way, for example, that the product obtained from drying is brought into contact with the solid catalyst in suspension. The rearrangement can be performed batchwise or continuously in a stirred-tank reactor, a series of stirred-tank reactors, in a tubular reactor (e.g. fixed-bed or fluidised-bed reactor) or in a combination thereof. Serial fixed catalyst beds are advantageously used. A mixture of aminobenzylanilines, aniline and small quantities of diaminophenylmethanes is first obtained in a temperature range of 20 to 70° C., preferably 40 to 60° C., depending on the catalyst used. To this end, the reaction mixture is preferably pumped over the fixed catalyst bed, whereby residence times of 0.2 to 2 hours are typically set. The optimum temperature for a selected catalyst and a desired isomer ratio in the aminobenzylanilines obtained is easily determined by means of preliminary tests.

In the continuing process the further rearrangement of the aminobenzylanilines to the MDA isomers is performed at an increased temperature of 70 to 140° C., preferably 90 to 130° C., whereby residence times of 0.2 to 2 hours are typically set. In this case too a catalyst bed is used as the particularly preferred embodiment, although all other above-mentioned methods can also be used.

In the continuing process the rearrangement of any residual aminobenzylanilines to MDA isomers can if necessary be performed at a further increased temperature of 130 to 200° C., preferably 140 to 175° C., without MDA polymers being formed in significant quantities or considerable quantities of 4,4'-MDA being isomerised to ortho isomers. To this end, residence times of 0.02 to 2 hours, preferably 0.1 to 1 hour, are typically set in an additional catalyst bed.

On completion of the reaction, the reaction mixture obtained by the process according to the invention can be processed in a step (c) such that the excess aniline optionally contained in the mixture can be separated from the MDA isomers either continuously or batchwise by known methods such as distillation or crystallisation, for example, and recycled. The MDA isomers are then sent for subsequent phosgenation.

It is surprising that low-polymer MDA grades with a high proportion of 4,4'-isomer can be obtained by this process and that commercial Y zeolites can be used as catalysts for this process without their first having to undergo a modification, e.g. fluorination. It is particularly surprising that by varying the temperature and/or the catalyst type in the first reaction phase (a), the p-isomer content can be selectively controlled and the o-isomer content (2,4'-MDA and 2,2'-MDA) minimised to a maximum of 20 wt. %, preferably a maximum of 18 wt. %, particularly preferably a maximum of 16 wt. % (relative to the total quantity of binuclear compounds).

The product properties obtained by the process according to the invention are adjusted by combining the process parameters of temperature, A/F ratio, and particularly by choosing the zeolite with the optimum activity in the selected temperature window, as shown in the following examples.

The present invention is illustrated by means of the following examples, but is in no way restricted to these examples. The examples are intended in particular to help the person skilled in the art to select suitable catalysts for the desired version of the process and to determine the optimum temperature progression for a selected catalyst.

EXAMPLES

Example 1

300 g aniline and 33.6 g aqueous formaldehyde solution (32 wt. % formaldehyde in water) corresponding to a molar ratio of A/F=9 are placed together in a batch reactor under protective gas, whereby at a temperature of 60° C. the formation of aminal is initiated spontaneously and without catalysis. After the reaction mixture is transferred to a separating funnel, phase separation begins and the organic phase is separated off and subjected to an additional drying.

This drying was performed in various ways, whereby the selected method had no significant influence on the final result:

a) by means of drying agents:
50 g of a dry zeolite (molecular sieve 4 Å, Bayer AG) is added to the moist aminal phase (170 g) at approx. 60–80° C. and the solution standing above the molecular sieve is stirred for approx. 1 h. The organic phase dried in this way is clear and light brown in colour and has an average water content determined by the Karl Fischer method of <0.05%.

b) by means of batch distillation:
The aqueous aminal emulsion (527.5 g) with a water content of approx. 5 wt. % is dehydrated by batchwise distillation through a water separator under reflux in a 1000 ml flask at a pressure of 100 hPa. Distillation is initially performed at an overhead temperature of approx. 50° C. which, as the water concentration in the aminal falls, must be increased to a maximum overhead temperature of 110 to 115° C. with a bottoms temperature of 117 to 120° C. In the water separator the water and aniline phase of the condensate are separated and the aniline phase returned to the flask. An average water content of approx. 0.04 % was determined in the clear, pale-brown solution from the bottoms (460 g) according to the Karl Fischer method.

c) by means of continuous distillation:
The aqueous aminal emulsion with a water content of approx. 5 wt. % is dehydrated by continuous distillation in a rectifying column. The moist aminal from the column at an overhead pressure of 100 mbar, for example, and a corresponding overhead temperature of 48° C. is supplied as feed at 100 g/h such that a water-aniline azeotrope can be continuously removed from the top at 18 g/h and the practically anhydrous aminal removed from the foot at 82 g/h. An average water content of approx. 0.04% was determined in the clear, pale-brown withdrawal from the bottoms according to the Karl Fischer method.

Example 2 a) The aminal produced and dried according to example 1 a) is reacted in a discontinuous experimental arrangement with a commercial H—Y zeolite extrudate (DEGUSSA WESSALITH® DAY F 20, Degussa AG) activated at 300° C. for 15 h. 15 g of the activated moulded catalyst is used for 100 g dry aminal. The reaction is then performed in a temperature-graduated operation at 50° C. for 6 h and then at 130° C. for 4 h and the reaction mixture analysed by HPLC. The final intermediate residues (aminobenzylanilines) are depleted in the high-temperature phase within the analytical detection limit. An MDA having a composition of 98 mol % monomeric MDA and 2 mol % polynuclear compounds relative to the aniline-free mixture is obtained. The o-isomer content is 14 mol %.

b) Similarly to example 2 A), the same quantities are reacted under comparable apparatus conditions, except that the temperature is not graduated and the reaction is instead performed isothermally at 130° C. After the final intermediate residues (aminobenzylanilines) have depleted completely within the analytical detection limit, an MDA having a composition of 91 mol % monomeric MDA and 9 mol % polynuclear compounds relative to the aniline-free mixture is obtained. The o-isomer content is 21 mol %.

Example 3

The aminal produced and dried according to example 1 a) is reacted in a forced circulation experiment with a commercial H—Y zeolite extrudate (WESSALITH® DAY F 20, Degussa AG) that has previously been activated at 300° C.

for 15 h. The dry aminal is passed over a bed of the activated catalyst, which is contained in a jacket-heated glass tube. In a first reactor the aminal is passed over the fixed bed consisting of 50 g catalyst at 50° C. and at a volumetric flow rate of approx. 60 ml/min and pumped back into the reactor, achieving a total running time of 90 min. In an identical reactor the reaction mixture is then pumped over the catalyst bed at 130° C. for 45 min. The final conditioning is performed at 150° C. for a further 30 min in an identical structure, whereby this final phase is intended purely as a security measure to ensure the complete depletion of the undesirable aminobenzylaniline intermediates. The final intermediate residues (aminobenzylanilines) are again depleted in the high-temperature phase within the analytical detection limit. An MDA having a composition of 97 mol % monomeric MDA and 3% polynuclear compounds is obtained. The o-isomer content is 14%.

Example 4

In the same way as in example 3, each graduation (50→130→150° C.) is performed in succession for 20 identical reaction cycles using freshly prepared aminal, whereby the following conversions (in % of theoretical yield) and selectivities were observed as a function of the running time.

|  | Run | | | |
| --- | --- | --- | --- | --- |
|  | 3 | 7 | 13 | 20 |
| 4,4'-MDA: | 84.1% | 83.4% | 84.0% | 84.8% |
| 2,4-MDA: | 13.5% | 12.7% | 12.9% | 14.6% |

Example 5

The aminal produced and dried according to example 1 b) is reacted with a commercial H—Y zeolite extrudate (WESSALITH® DAY F 20, Si/Al=23, Degussa AG) that has previously been activated at 300° C. for 15 h. The dry aminal solution is passed at a mass flow rate of 180 g/h over a bed of catalyst (72 g) contained in a jacket-heated glass tube (200×30 mm). With this design of catalyst bed, only a partial rearrangement of the aminal solution used (approx. 50% of theoretical) is to be expected below the selected reaction temperature of T=50° C. Samples of the emerging flow of material are then taken at regular intervals in order to quantify the activity of the catalyst according to the reaction time. These are analysed in terms of conversion by means of HPLC. The following aminal conversions to the corresponding rearrangement products (aminobenzylanilines, MDA) after a catalyst service life of 24 h were determined according to the content of aliphatic amines in the aniline used:

| Aliphatic amines (ppm) | Conversion (% of theoretical) |
| --- | --- |
| <5 | 62% |
| 15 | 43% |
| 60 | 23% |
| 1000 | <1% |

Example 6

As in the experiment described in example 5, several fixed beds with a catalyst bed are operated in series at increasing temperatures. The dry aminal solution is passed at a mass flow rate of 180 g/h over a series of three connected beds, each comprising 72 g of the catalyst WESSALITH® DAY F 20, Degussa AG, which in each case is contained in jacket-heated glass tubes (200×30 mm) at a temperature of 50° C. The reaction mixture then flows through a series of two fixed beds of identical design (2×72 g of the same catalyst), which are operated at 130° C. Finally it is passed through a fixed bed of the same design heated to 150° C. (72 g of the same catalyst). Samples of the emerging flow of material are then taken at regular intervals in order to quantify the activity of the catalyst according to the reaction time. These are analysed in terms of conversion by means of HPLC.

In this way, using aniline with a cyclohexylamine content of approx. 15 ppm, an MDA having a composition of 98 mol % monomeric MDA and 2 mol % polynuclear compounds relative to the aniline-free mixture is obtained unchanged over a continuous total operating period of 5 days. The o-isomer content is 10 mol %.

What is claimed is:

1. A process for the production of methylenedianilines comprising (1) condensing aniline which contains less than 100 ppm aliphatic amines, and a methylene group-supplying agent, at a molar ratio of aniline to methylene group-supplying agent of 1.7:1 to 100:1 to form a condensate of aniline and the methylene group-supplying agent; (2) drying the condensate of aniline and the methylene group-supplying agent; and (3) rearranging the dried condensate under gentle conditions in the presence of solid, inorganic, acid catalysts to form low-polymer methylenedianiline with a predominant 4,4'-isomer content.

2. The process according to claim 1, wherein said rearranging of the dried condensate is performed in at least two stages at a temperature that increases between the stages.

3. The process according to claim 1, wherein said aniline contains less than 25 ppm aliphatic amines.

4. The process according to claim 1, wherein the catalysts are selected from the group consisting of powdered zeolites and zeolite mouldings in the $H^+$ form, which are present in suspension or as fixed beds.

5. The process according to claim 1, wherein said rearranging is performed batchwise in a stirred-tank reactor, continuously in a stirred-tank reactor, in a series of stirred-tank reactors, in a tubular reactor, in a fixed-bed reactor, in a fluidized-bed reactor or in a combination thereof.

6. The process according to claim 1, wherein the condensate of aniline and the methylene group-supplying agent comprises an aminal or a solution thereof that contains less than 1000 ppm water.

7. The process according to claim 1, wherein said catalysts comprise FAU zeolites.

* * * * *